(12) United States Patent
Burgermeister et al.

(10) Patent No.: US 7,914,573 B2
(45) Date of Patent: Mar. 29, 2011

(54) POLYMERIC STENT HAVING MODIFIED MOLECULAR STRUCTURES

(75) Inventors: Robert Burgermeister, Bridgewater, NJ (US); Joseph H. Contiliano, Stewartsville, NJ (US); Vipul Dave, Hillsborough, NJ (US); Yufu Li, Bridgewater, NJ (US); Pallassana V. Narayanan, Belle Mead, NJ (US); David W. Overaker, Annandale, NJ (US); Qiang Zhang, Annandale, NJ (US)

(73) Assignee: Cordis Corporation, Miami Lakes, FL (US)

( * ) Notice: Subject to any disclaimer, the term of this patent is extended or adjusted under 35 U.S.C. 154(b) by 786 days.

(21) Appl. No.: 11/440,770

(22) Filed: May 25, 2006

(65) Prior Publication Data

US 2007/0134289 A1 Jun. 14, 2007

Related U.S. Application Data

(63) Continuation-in-part of application No. 11/301,883, filed on Dec. 13, 2005, now abandoned.

(51) Int. Cl.
*A61F 2/06* (2006.01)
(52) U.S. Cl. ...................... 623/1.42; 623/1.49
(58) Field of Classification Search .............. 623/1.15, 623/1.16, 1.32, 1.18, 1.19, 1.2, 1.49, 1.42
See application file for complete search history.

(56) References Cited

U.S. PATENT DOCUMENTS

| 5,516,781 | A | * | 5/1996 | Morris et al. | 514/291 |
| 5,670,161 | A | | 9/1997 | Healy et al. | |
| 2002/0049489 | A1 | * | 4/2002 | Herweck et al. | 623/1.13 |
| 2002/0072792 | A1 | * | 6/2002 | Burgermeister et al. | 623/1.16 |
| 2004/0148014 | A1 | | 7/2004 | Nuutinen et al. | |
| 2005/0137678 | A1 | * | 6/2005 | Varma | 623/1.15 |
| 2005/0187615 | A1 | | 8/2005 | Williams et al. | |
| 2006/0020330 | A1 | * | 1/2006 | Huang et al. | 623/1.49 |

FOREIGN PATENT DOCUMENTS

| EP | 1452151 B1 | 10/2008 |
| WO | WO 03/034940 A2 | 5/2003 |
| WO | WO 03/094798 A1 | 11/2003 |

OTHER PUBLICATIONS

International Search Report for related Application No. 06256289.7-2310 dated Jul. 16, 2007.

* cited by examiner

*Primary Examiner* — David Isabella
*Assistant Examiner* — Suba Ganesan
(74) *Attorney, Agent, or Firm* — Carl J. Evens

(57) ABSTRACT

A biocompatible material may be configured into any number of implantable medical devices including intraluminal stents. Polymeric materials may be utilized to fabricate any of these devices, including stents. The stents may be balloon expandable or self-expanding. By preferential mechanical deformation of the polymer, the polymer chains may be oriented to achieve certain desirable performance characteristics.

4 Claims, 12 Drawing Sheets

|   | Draw Ratio | Yield Strength (MPa) | Tensile Modulus (GPa) |
|---|---|---|---|
| 1 | 1x | 58 | 2.8 |
| 2 | 1.4x | 52 | 3.4 |
| 3 | 1.8x | 56 | 3.8 |
| 4 | 2.1x | 56 | 3.8 |
| 5 | 2.2x | 55 | 3.6 |
| 6 | 2.4x | 59 | 3.2 |
| 7 | 2.5x | 63 | 4.0 |
| 8 | 2.6x | 67 | 4.3 |
| 9 | 2.7x | 68 | 4.3 |
| 10 | 2.8x | 76 | 4.5 |

| | Draw Ratio | Yield Strength (MPa) | Tensile Modulus (GPa) |
|---|---|---|---|
| 1 | 1x | 59 | 3.3 |
| 2 | 1.6x | 70 | 2.8 |
| 3 | 1.8x | 69 | 3.3 |
| 4 | 2.2x | 77 | 3.8 |
| 5 | 2.8x | 110 | 3.9 |

POLYMERIC STENT HAVING MODIFIED MOLECULAR STRUCTURES

CROSS-REFERENCE TO RELATED APPLICATIONS

This patent application is a continuation-in-part of U.S. patent application Ser. No. 11/301,883 filed Dec. 13, 2005 now abandoned, the contents of which are incorporated herein by reference.

BACKGROUND OF THE INVENTION

1. Field of the Invention

The present invention relates to intraluminal polymeric stents, and more particularly to intraluminal polymeric stents having a modified molecular orientation due to the application of stress.

2. Discussion of the Related Art

Currently manufactured intraluminal stents do not adequately provide sufficient tailoring of the properties of the material forming the stent to the desired mechanical behavior of the device under clinically relevant in-vivo loading conditions. Any intraluminal device should preferably exhibit certain characteristics, including maintaining vessel patency through an acute and/or chronic outward force that will help to remodel the vessel to its intended luminal diameter, preventing excessive radial recoil upon deployment, exhibiting sufficient fatigue resistance and exhibiting sufficient ductility so as to provide adequate coverage over the full range of intended expansion diameters.

Accordingly, there is a need to develop materials and the associated processes for manufacturing intraluminal stents that provide device designers with the opportunity to engineer the device to specific applications.

SUMMARY OF THE INVENTION

The present invention overcomes the limitations of applying conventionally available materials to specific intraluminal therapeutic applications as briefly described above.

In accordance with one embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being greater than the second amount of alignment, and a plurality of bridges formed from a polymeric material interconnecting the plurality of hoops.

In accordance with another embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being less than the second amount of alignment, and a plurality of bridges formed from a polymeric material interconnecting the plurality of hoops.

In accordance with another embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being substantially equal to the second amount of alignment, and a plurality of bridges formed from a polymeric material interconnecting the plurality of hoops.

In accordance with another embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being greater than the second amount of alignment, the plurality of hoops being interconnected to form the substantially tubular structure.

In accordance with another embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being less than the second amount of alignment, the plurality of hoops being interconnected to form the substantially tubular structure.

In accordance with another embodiment, the present invention is directed to a substantially tubular intraluminal medical device having a longitudinal axis and a radial axis. The device comprising a plurality of hoops formed from a polymeric material, the plurality of hoops comprising a plurality of radial struts and a plurality of radial arcs, the plurality of radial struts having a first amount of alignment of the polymer chains comprising the polymeric material in a direction substantially parallel to the longitudinal axis and the plurality of radial arcs having a second amount of alignment of the polymer chains comprising the polymeric material in a direction substantially parallel to the radial axis, the first amount of alignment being substantially equal to the second amount of alignment, the plurality of hoops being interconnected to form the substantially tubular structure.

The biocompatible materials for implantable medical devices of the present invention may be utilized for any number of medical applications, including vessel patency devices such as vascular stents, biliary stents, ureter stents, vessel occlusion devices such as atrial septal and ventricular septal occluders, patent foramen ovale occluders and orthopedic devices such as fixation devices.

The biocompatible materials of the present invention comprise a unique composition and designed-in properties that enable the fabrication of stents that are able to withstand a broader range of loading conditions than currently available stents. More particularly, the molecular structure designed into the biocompatible materials facilitates the design of stents with a wide range of geometries that are adaptable to various loading conditions.

The intraluminal devices of the present invention may be formed out of any number of biocompatible polymeric materials. In order to achieve the desired mechanical properties, the polymeric material, whether in the raw state or in the tubular or sheet state may be physically deformed to achieve a certain degree of alignment of the polymer chains. This alignment may be utilized to enhance the physical and/or mechanical properties of one or more components of the stent.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Implantable medical devices may be fabricated from any number of suitable biocompatible materials, including polymeric materials. The internal structure of these polymeric materials may be altered utilizing mechanical and/or chemical manipulation of the polymers. These internal structure modifications may be utilized to create devices having specific gross characteristics such as crystalline and amorphous morphology and orientation as is explained in detail subsequently. Although the present invention applies to any number of implantable medical devices, for ease of explanation, the following detailed description will focus on an exemplary stent.

Figure 1:
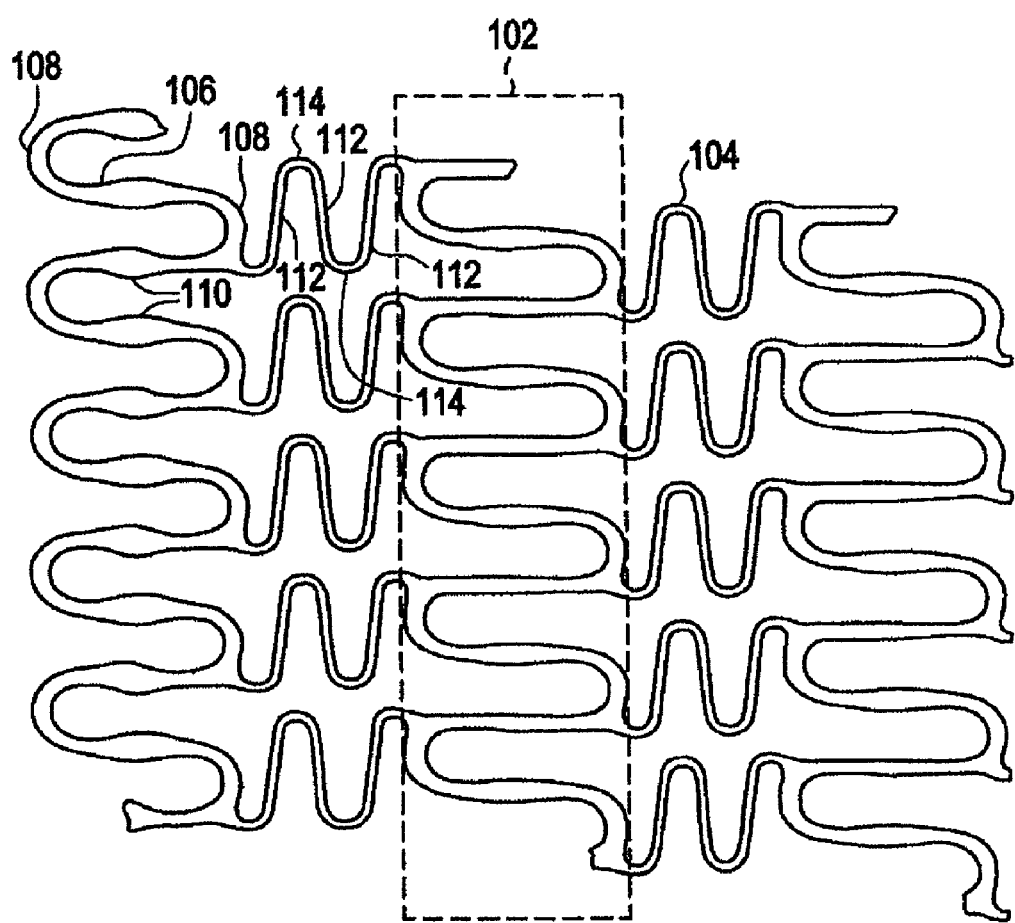
FIG. 1 is a planar representation of an exemplary stent fabricated from biocompatible materials in accordance with the present invention.

Referring to FIG. 1, there is illustrated a partial planar view of an exemplary stent 100 in accordance with the present invention. The exemplary stent 100 comprises a plurality of hoop components 102 interconnected by a plurality of flexible connectors 104. The hoop components 102 are formed as a continuous series of substantially longitudinally or axially oriented radial strut members 106 and alternating substantially circumferentially oriented radial arc members 108. Although shown in planar view, the hoop components 102 are essentially ring members that are linked together by the flexible connectors 104 to form a substantially tubular stent structure. The combination of radial strut members 106 and alternating radial arc members 108 form a substantially sinusoidal pattern. Although the hoop components 102 may be designed with any number of design features and assume any number of configurations, in the exemplary embodiment, the radial strut members 106 are wider in their central regions 110. This design feature may be utilized for a number of purposes, including, increased surface area for drug delivery.

The flexible connectors 104 are formed from a continuous series of flexible strut members 112 and alternating flexible arc members 114. The flexible connectors 104, as described above, connect adjacent hoop components 102 together. In this exemplary embodiment, the flexible connectors 104 have a substantially N-shape with one end being connected to a radial arc member on one hoop component and the other end being connected to a radial arc member on an adjacent hoop component. As with the hoop components 102, the flexible connectors 104 may comprise any number of design features and any number of configurations. In the exemplary embodiment, the ends of the flexible connectors 104 are connected to different portions of the radial arc members of adjacent hoop components for ease of nesting during crimping of the stent. It is interesting to note that with this exemplary configuration, the radial arcs on adjacent hoop components are slightly out of phase, while the radial arcs on every other hoop component are substantially in phase. In addition, it is important to note that not every radial arc on each hoop component need be connected to every radial arc on the adjacent hoop component.

It is important to note that any number of designs may be utilized for the flexible connectors or connectors in an intraluminal scaffold or stent. For example, in the design described above, the connector comprises two elements, substantially longitudinally oriented strut members and flexible arc members. In alternate designs, however, the connectors may comprise only a substantially longitudinally oriented strut member and no flexible arc member or a flexible arc connector and no substantially longitudinally oriented strut member.

The substantially tubular structure of the stent 100 provides either temporary or permanent scaffolding for maintaining patency of substantially tubular organs, such as arteries. The stent 100 comprises a luminal surface and an abluminal surface. The distance between the two surfaces defines the wall thickness. The stent 100 has an unexpanded diameter for delivery and an expanded diameter, which roughly corresponds to the normal diameter of the organ into which it is delivered. As tubular organs such as arteries may vary in diameter, different size stents having different sets of unexpanded and expanded diameters may be designed without departing from the spirit of the present invention. As described herein, the stent 100 may be formed form any number of polymeric materials.

Accordingly, in one exemplary embodiment, an intraluminal scaffold element may be fabricated from a non-metallic material such as a polymeric material including non-crosslinked thermoplastics, cross-linked thermosets, composites and blends thereof. There are typically three different forms in which a polymer may display the mechanical properties associated with solids; namely, as a crystalline structure, as a semi-crystalline structure and/or as an amorphous structure. All polymers are not able to fully crystallize, as a high degree of molecular regularity within the polymer chains is essential for crystallization to occur. Even in polymers that do crystallize, the degree of crystallinity is generally less than one hundred percent. Within the continuum between fully crystalline and amorphous structures, there are two thermal transitions possible; namely, the crystal-liquid transition (i.e. melting point temperature, $T_m$) and the glass-liquid transition (i.e. glass transition temperature, $T_g$). In the temperature range between these two transitions there may be a mixture of orderly arranged crystals and chaotic amorphous polymer domains.

The Hoffman-Lauritzen theory of the formation of polymer crystals with "folded" chains owes its origin to the discovery in 1957 that thin single crystals of polyethylene may be grown from dilute solutions. Folded chains are preferably required to form a substantially crystalline structure. Hoffman and Lauritzen established the foundation of the kinetic theory of polymer crystallization from "solution" and "melt" with particular attention to the thermodynamics associated with the formation of chain-folded nuclei.

Crystallization from dilute solutions is required to produce single crystals with macroscopic perfection (typically magnifications in the range of about 200× to about 400×). Polymers are not substantially different from low molecular weight compounds such as inorganic salts in this regard. Crystallization conditions such as temperature, solvent and solute concentration may influence crystal formation and final form. Polymers crystallize in the form of thin plates or "lamellae." The thickness of these lamellae is on the order of 10 nanometers (i.e. nm). The dimensions of the crystal plates perpendicular to the small dimensions depend on the conditions of the crystallization but are many times larger than the thickness of the platelets for a well-developed crystal. The chain direction within the crystal is along the short dimension of the crystal, which indicates that, the molecule folds back and forth (e.g. like a folded fire hose) with successive layers of folded molecules resulting in the lateral growth of the platelets. A crystal does not consist of a single molecule nor does a molecule reside exclusively in a single crystal. The loop formed by the chain as it emerges from the crystal turns around and reenters the crystal. The portion linking the two crystalline sections may be considered amorphous polymer. In addition, polymer chain ends disrupt the orderly fold patterns of the crystal, as described above, and tend to be excluded from the crystal. Accordingly, the polymer chain ends become the amorphous portion of the polymer. Therefore, no currently known polymeric material can be 100 percent crystalline. Post polymerization processing conditions dictate the crystal structure to a substantial extent.

Single crystals are not observed in crystallization from bulk processing. Bulk crystallized polymers from melt exhibits domains called "spherulites" that are symmetrical around a center of nucleation. The symmetry is perfectly circular if the development of the spherulite is not impinged by contact with another expanding spherulite. Chain folding is an essential feature of the crystallization of polymers from the molten state. Spherulites are composed of aggregates of "lamellar" crystals radiating from a nucleating site. Accordingly, there is a relationship between solution and bulk grown crystals.

The spherical symmetry develops with time. Fibrous or lathlike crystals begin branching and fanning out as in dendritic growth. As the lamellae spread out dimensionally from the nucleus, branching of the crystallites continue to generate the spherical morphology. Growth is accomplished by the addition of successive layers of chains to the ends of the radiating laths. The chain structure of polymer molecules suggests that a given molecule may become involved in more than one lamella and thus link radiating crystallites from the same or adjacent spherulites. These interlamellar links are not possible in spherulites of low molecular weight compounds, which show poorer mechanical strength as a consequence.

The molecular chain folding is the origin of the "Maltese" cross, which identifies the spherulite under crossed polarizers. For a given polymer system, the crystal size distribution is influenced by the initial nucleation density, the nucleation rate, the rate of crystal growth, and the state of orientation. When the polymer is subjected to conditions in which nucleation predominates over radial growth, smaller crystals result. Larger crystals will form when there are relatively fewer nucleation sites and faster growth rates. The diameters of the spherulites may range from about a few microns to about a few hundred microns depending on the polymer system and the crystallization conditions.

Therefore, spherulite morphology in a bulk-crystallized polymer involves ordering at different levels of organization; namely, individual molecules folded into crystallites that in turn are oriented into spherical aggregates. Spherulites have been observed in organic and inorganic systems of synthetic, biological, and geological origin including moon rocks and are therefore not unique to polymers.

Stress induced crystallinity is important in film and fiber technology. When dilute solutions of polymers are stirred rapidly, unusual structures develop which are described as having "shish kebab" morphology. These consist of chunks of folded chain crystals strung out along a fibrous central column. In both the "shish" and the "kebab" portions of the structure, the polymer chains are parallel to the overall axis of the structure.

When a polymer melt is sheared and quenched to a thermally stable condition, the polymer chains are perturbed from their random coils to easily elongate parallel to the shear direction. This may lead to the formation of small crystal aggregates from deformed spherulites. Other morphological changes may occur, including spherulite to fibril transformation, polymorphic crystal formation change, reorientation of already formed crystalline lamellae, formation of oriented crystallites, orientation of amorphous polymer chains and/or combinations thereof.

Molecular orientation is important as it primarily influences bulk polymer properties and therefore will have a strong effect on the final properties that are essential for different material applications. Physical and mechanical properties such as permeability; wear; refractive index; absorption; degradation rates; tensile strength; yield stress; tear strength; modulus and elongation at break are some of the properties that will be influenced by orientation. Orientation is not always favorable as it promotes anisotropic behavior. Orientation can occur in several directions such as uniaxial, biaxial and multiaxial. It can be induced by drawing, rolling, calendaring, spinning, blowing, etc and is present in systems including fibers; films; tubes; bottles; molded and extruded articles; coatings; and composites. When a polymeric material is processed, there will be preferential orientation in a specific direction. Usually it is in the direction in which the process is conducted and is called machine direction (MD). Many of the products are purposely oriented to provide improved properties in a particular direction. If a product is melt processed, it will have some degree of preferential orientation. In case of solvent processed materials, orientation may be induced during processing by methods such as shearing the polymer solution followed by immediate precipitation or quenching to the desired geometry in order to lock in the orientation during the shearing process. Alternately, if the polymers have rigid rod like chemical structure then it will orient during processing due to the liquid crystalline morphology in the polymer solution.

The orientation state will depend on the type of deformation and the type of polymer. Even though a material is highly deformed or drawn, it is not necessary to impart high levels of orientation as the polymer chains can relax back to its original state. This generally occurs in polymers that are very flexible at the draw temperature. Therefore, several factors may influence the state of orientation in a given polymer system including rate of deformation (e.g., strain rate; shear rate; frequency; etc); amount of deformation (draw ratio); temperature; molecular weight and its distribution; chain configuration (e.g., stereoregularity; geometrical isomers; etc); chain architecture (linear; branched; cross-linked; dendritic etc); chain stiffness (flexible; rigid; semi-rigid; etc); copolymer types (random; block; alternating; etc); and presence of additives (plasticizers; hard and soft fillers; long and short fibers; therapeutic agents; blends; etc).

Since polymers consist of two phases; namely, crystalline and amorphous, the effect of orientation will differ for these phases, and therefore the final orientation may not be the same for these two phases in a semi-crystalline polymer system. This is because the flexible amorphous chains will respond differently to the deformation and the loading conditions than the hard crystalline phase.

Different phases can be formed after inducing orientation and its behavior depends on the chemistry of the polymer backbone. A homogenous state such as a completely amorphous material would have a single orientation behavior. However, in polymers that are semi-crystalline, block copolymers or composites (fiber reinforced; filled systems, liquid crystals), the orientation behavior needs to be described by more than one parameter. Orientation behavior, in general, is directly proportional to the material structure and orientation conditions. There are several common levels of structure that exist in a polymeric system such as crystalline unit cell; lamellar thickness; domain size; spherulitic structures; oriented superstructures; phase separated domains in polymer blends; etc.

For example, in extruded polyethylene, the structure is a stacked folded chain lamellar structure. The orientation of the lamellae within the structure is along the machine direction, however the platelets are oriented perpendicular to the machine direction. The amorphous structure between the lamellae is generally not oriented. Mechanical properties of the material will be different when tested in different directions (0 degree to the machine direction, 45 degrees to the machine direction and 90 degrees to the machine direction). The elongation values are usually lowest when the material is stretched in machine direction. When stretched at 45 degrees to the machine direction, shear deformation occurs of the lamellae and will provide higher elongation values. When stretched at 90 degrees to the machine direction, the material will exhibit highest elongation as the chain axis is unfolding.

When a polymer chain is oriented at an angle with respect to a given deformation axis, the orientation of the chain can be defined by Hermans orientation function f which varies from 1, $-\frac{1}{2}$ and 0 representing perfect orientation, perpendicular orientation, and random orientation along the axis, respectively. This applies mainly to uniaxially oriented systems. There are several techniques used to measure orientation such as birefringence; linear dichroism; wide angle x-ray scattering; polarized Raman scattering; polarized fluorescence; and NMR.

The stents of the current invention can be prepared from different processes such as melt and solution. Typical melt processes include injection molding, extrusion, fiber spinning, compression molding, blow molding, pultrusion, etc. Typical solution processes include solvent cast tubes and films, electrostatic fiber spinning, dry and wet spinning, hollow fiber and membrane spinning, spinning disk, etc. Pure polymers, blends, and composites can be used to prepare the stents. The precursor material can be a tube or a film that is prepared by any of the processes described above, followed by laser cutting. The precursor material can be used as prepared or can be modified by annealing, orienting or relaxing them under different conditions. Alternately, the laser cut stent can be used as prepared or can be modified by annealing, orienting or relaxing them under different conditions.

The effect of polymer orientation in a stent or device can improve the device performance including radial strength, recoil, and flexibility. Orientation can also vary the degradation time of the stent, so as desired, different sections of the stents can be oriented differently. Orientation can be along the axial and circumferential or radial directions as well as any other direction in the unit cell and flex connectors to enhance the performance of the stent in those respective directions. The orientation may be confined to only one direction (uniaxial), may be in two directions (biaxial) and/or multiple directions (multiaxial). The orientation may be introduced in a given material in different sequences, such as first applying axial orientation followed by radial orientation and vice versa. Alternately, the material may be oriented in both directions at the same time. Axial orientation may be applied by stretching along an axial or longitudinal direction in a given material such as tubes or films at temperatures usually above the glass transition temperature of the polymer. Radial or circumferential orientation may be applied by several different methods such as blowing the material by heated gas for example, nitrogen, or by using a balloon inside a mold. Alternately, a composite or sandwich structure may be formed by stacking layers of oriented material in different directions to provide anisotropic properties. Blow molding may also be used to induce biaxial and/or multiaxial orientation.

Stents for balloon expandable applications preferably require a material with sufficient elongation at break to allow the stent to be crimped in a low profile state for insertion into the vasculature, while also enabling the stent to withstand the excessive strains during balloon expansion without damage. It is further preferable to have a material with improved elongation at break, i.e. ultimate strain capacity, without compromise to the modulus or ultimate strength of the material necessary to afford the stent sufficiently high radial strength with minimal stent recoil. Methods to increase elongation at break while maintaining or even improving material strength and stiffness, allow the stent thickness to be kept small, thereby resulting in better device flexibility and less resistance to impede blood flow. Traditional implantable absorbable polymers PLA, PGA, and copolymers of the PLA and PGA (PLGA) have relatively low elongation at break, approximately five to ten percent, with lower tensile strength and modulus compared to metal alloys (316L stainless steel and CoCr alloy L605) currently utilized to manufacture balloon expandable stents. These metal alloys typically possess an elongation at break of approximately forty percent, thus allowing stents from such materials to deploy under balloon pressure without breaking.

Prior art examples to increase the elongation at break of absorbable polymer based materials have included blending one or more elastomeric or low melting plasticizer components, typically in the range from about five to about twenty-five percent by weight. A potential disadvantage to such an approach is that tensile strength and/or modulus are typically compromised to some degree, thus reducing stent radial strength/stiffness. In addition the risk of increased creep or higher elastic recoil is also a possibility. Accordingly, there is a need for a process to improve the elongation at break of certain polymer based materials while subsequently having the ability to increase or at least maintain without compromise, the material's tensile modulus and strength. It would further be preferable for such a material to perhaps comprise fillers for enhancing radiopacity, and the potential to elute a pharmaceutical agent or other bioactive agent or compound.

The material used for modified molecular orientation may be produced by any known processing means, including solvent casting, injection molding and extrusion with either interim (tube, film and billet) or final part geometry, for example, laser cut stents. The modified molecular orientation process typically comprises heating the material to some temperature between the glass transition temperature (Tg) and the melting temperature (Tm) of the material, most preferably to a temperature approximately ten to twenty degrees C. above the Tg of the material. For a PLGA material this may be a temperature of about seventy degrees C. Heating may be achieved through various known means in the art, including heated water bath, environmental chamber, induction heating, and IR radiation. Those skilled in the relevant art may recognize other means of heating that also fall within the scope of the present invention. The material is held at this temperature for a predetermined amount of time, dependent on a number of factors, including the material, the amount of crystallinity, and part geometry. For heating a PLGA tube approximately 1.5-2 mm in OD with a half millimeter wall thickness, the hold time may be about ten seconds in a seventy degree C. water bath.

After such time, force (drawing) is applied in the desired direction or directions to induce modified molecular orientation in that direction. Drawing may be done in one direction or in multiple directions either simultaneously or sequentially. The total amount of drawing may be achieved directly from an undrawn condition at a specific drawing rate or sequentially in stages up to some final specified amount and with varying drawing rates. The orientation may be also be performed by first overdrawing the material in one or more directions and controlling the relaxation of this material to some orientation level below the overdrawn condition while maintaining the piece at the same temperature. In addition, drawing may be done in a helical direction by drawing axially and rotating the part at the same time. This may be advantageous for a helical stent design to introduce orientation along the helical pitch axis.

The following examples illustrate the effects of the processes described above.

Example 1

Figure 8:
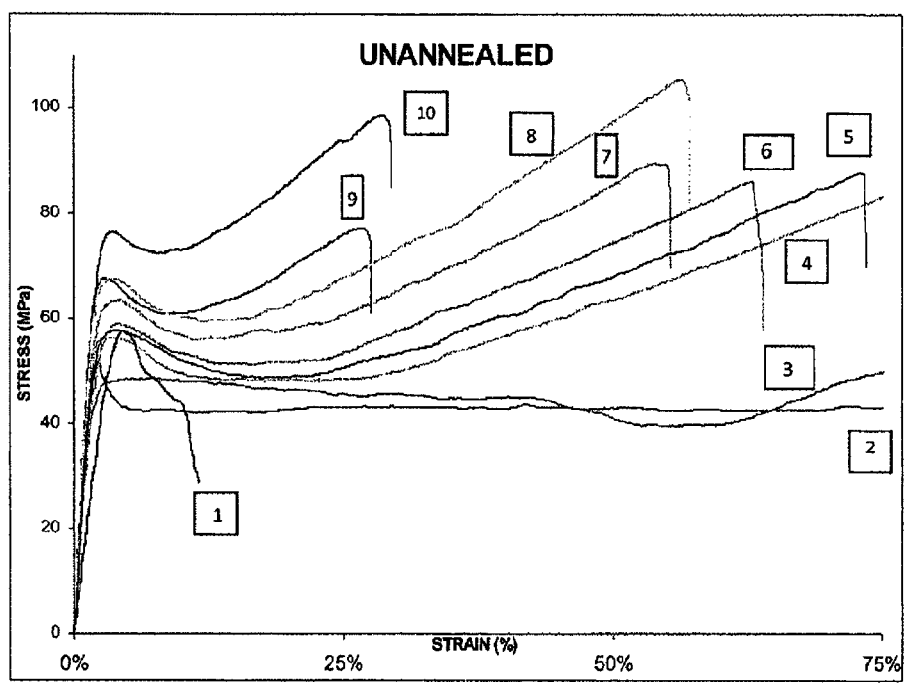
FIG. 8 is the data and graphical form of the yield strength and tensile modulus for a draw ratio ranging from 1× to 2.8× in accordance with a first example.

Example 1 illustrates the effects of orientation in the range of 1×-2.8× on test film tests specimens of amorphous PLGA roughly 0.010" thick. The yield strength and tensile modulus for a draw ratio ranging from 1× to 2.8× are depicted in FIG. 8, where draw ratio is defined as the final size/original size in that particular direction.

The drawing process may be used in combination with prior or subsequent heat treatment such as annealing to affect the morphological or crystal structure of the polymer and to further tailor the material properties.

Example 2

Figure 9:
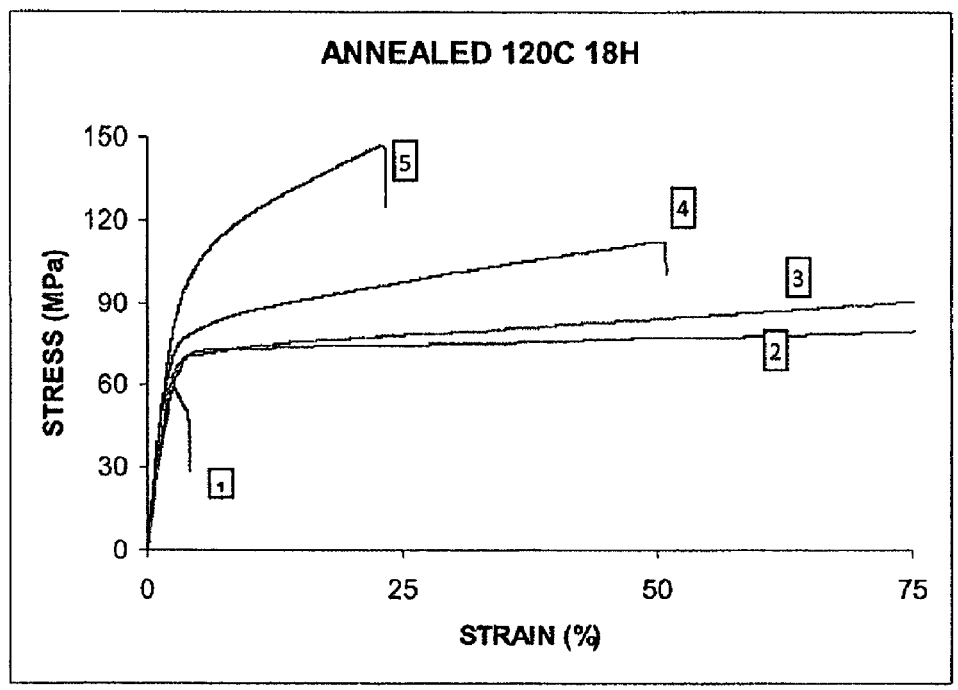
FIG. 9 is the data and graphical form of the yield strength and tensile modulus for a draw ratio ranging from 1× to 2.8× in accordance with a second example.

Example 2 illustrates the effects of orientation in the range of 1×-2.8× on 0.010" thick test film tests specimens of PLGA that were annealed for eighteen hours at one hundred twenty degrees C. to impart approximately twenty-five to thirty-five percent crystallinity to the material. The yield strength and tensile modulus for draw ratios ranging from 1× to 2.8× are depicted in FIG. 9.

Examples 1 and 2 demonstrate that regardless of being amorphous or semi-crystalline, elongation at break in the direction of alignment improves with orientation of the polymer chains. As draw levels increase the modulus, tensile strength, and affects of strain hardening also tend to increase while elongation at break begins to diminish, although still at significantly higher levels than undrawn samples. Those skilled in the arts may surmise by the trends shown in FIGS. 8 and 9 that there would be a theoretical upper limit in the amount of draw where excessive levels of draw above that depicted here could fracture the material or result in reduced elongation at break compared to the undrawn material.

Example 3

Figure 10:
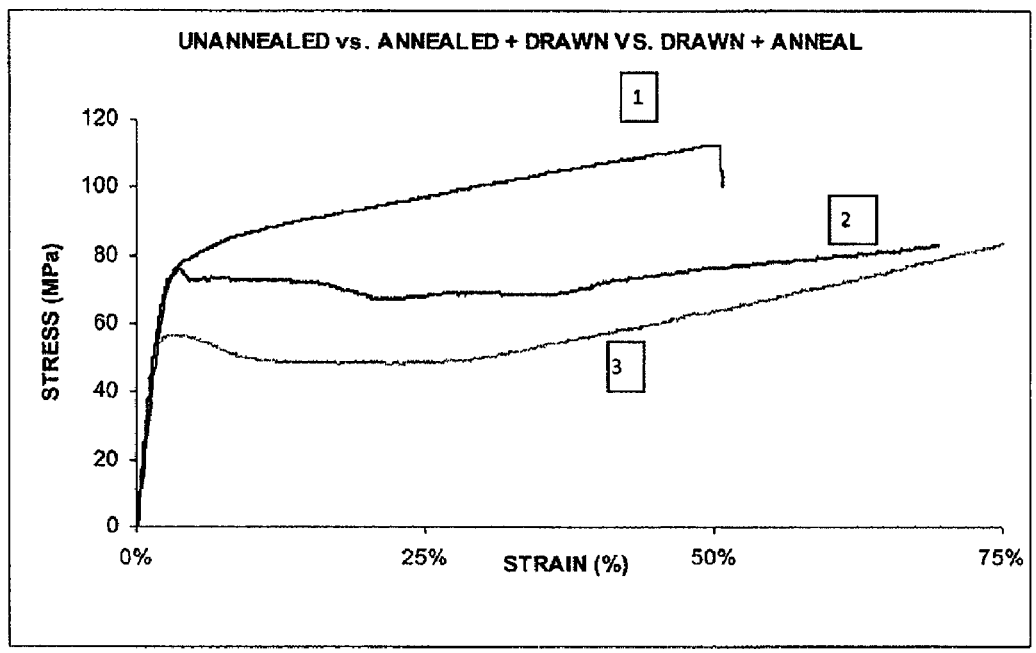
FIG. 10 is the data and graphical form of the stress-strain curves for PLGA in accordance with a third example.

The effect of annealing for one hundred twenty degrees C. for eighteen hours either before or after drawing 2.1× is graphically illustrated in FIG. 10 in the stress-strain curves for PLGA material compared to amorphous material that is just drawn 2.1×. Essentially, FIG. 10 illustrates that annealing or heat treatment in combination with drawing may improve the strength properties even further and that the order of drawing and annealing plays a role, particularly in the plastic region of the curve, or after the onset of yielding. Annealing following drawing may increase tensile strength and modulus while maintaining high elongation to break. Annealing before drawing may require higher forces necessary to draw the material (higher levels of crystallinity) and may result in higher levels of strain hardening.

Example 4

Figure 11:
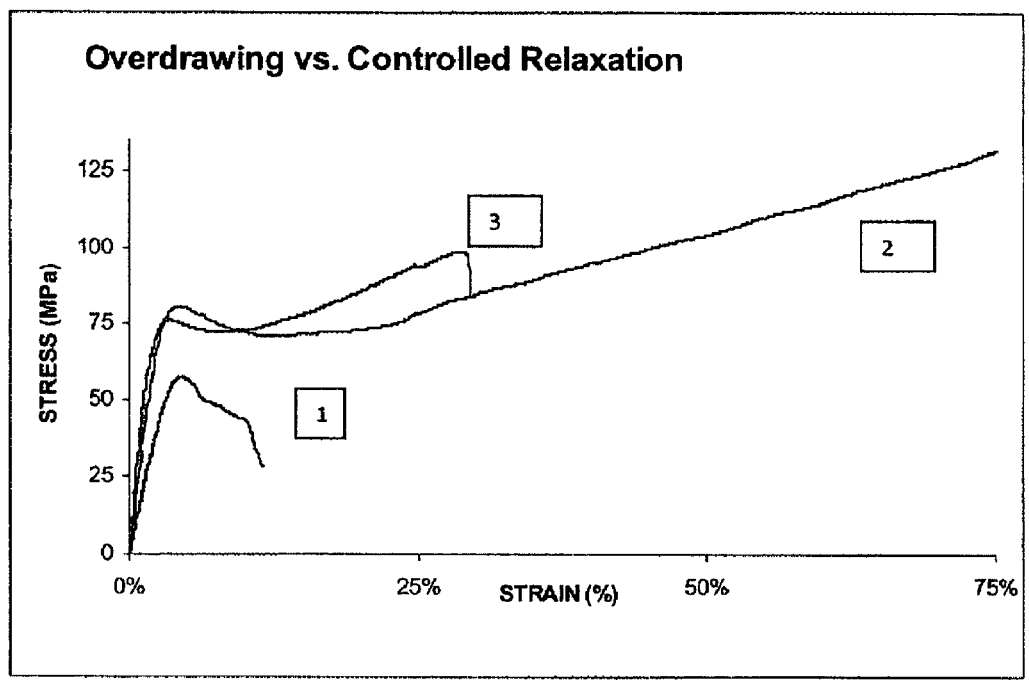
FIG. 11 is the data and graphical form of the stress-strain curves for PLGA in accordance with a fourth example.

PLGA compression molded film data demonstrates that when a film is first stretched to a certain level stretch ratio X1 and then allowed to return to a pre-determined stretch ratio X2, wherein x2 is less than x1, the tensile and modulus are comparable to that of directly stretched (to X2) films but the elongation at break is significantly enhanced. Overdrawing above a desired limit followed by controlled relaxation to a desired draw ratio may further enhance the elongation at break capability of the material, while maintaining tensile yield strength and modulus. The results are illustrated in FIG. 11.

An example of biaxial drawing on tubing may include first drawing the tube along its axis to a desired level then radially expanding the tube directly to final desired size by known means such as blow molding or overdrawing the tube diameter above the desired final size and reducing the internal pressure to allow the tube to relax to its final desired size. This may be before final machining of stent geometry, e.g. laser cutting, or even after stent geometry has been introduced. In this case the laser cutting would be done on the stent in the compressed state to provide the geometry desired after drawing. The size, shape and other parameters and the orientation processes are so designed that after the orientation step(s), the resulting stent has all required size, shape and other parameters as the final stent. The advantage here is that only parts (struts, connection parts, etc.) that needed to be oriented are actually oriented along the direction at which the parts will be deformed upon deployment, thus offering optimal properties.

Example 5

Figure 12:
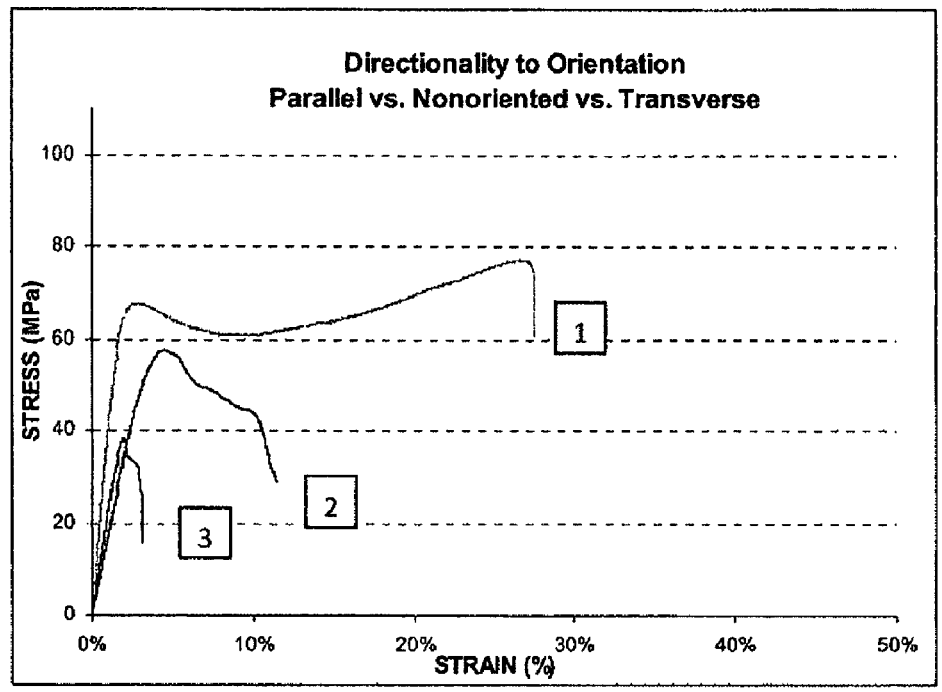
FIG. 12 is the data and graphical form of the stress-strain curves for PLGA in accordance with a fifth example.

Example 5 illustrates compression molded film samples of PLGA approximately 0.010" thick that were 1) drawn 2.75× parallel to test direction and 2) drawn 2.75× perpendicular to test direction and then compared to unoriented samples. The results are illustrated graphically, in FIG. 12.

The results show that for certain materials such as PLGA, orientation in one direction compromises material properties in the orthogonal direction to some degree. Therefore, a certain degree of biaxial orientation would be desirable so as to compensate for the drop in properties perpendicular to the uniaxial draw direction. Example 6 illustrates this point using oriented tubing to produce stents.

Example 6

Example 6 illustrates biaxial orientation of extruded PLGA tubing. Regarding direction of orientation for stent manufacture, the most preferred embodiment is biaxial orientation of tubing. Five groups of tubing were sequentially drawn, first axially followed by radially to the following degrees illustrated in Table 1 below.

TABLE 1

|  | Axial Draw | Radial Draw |
| --- | --- | --- |
| Group A | 2.5x | 1x |
| Group B | 1x | 1.4x |
| Group C | 1.9x | 1.2x |
| Group D | 2.2x | 1.2x |
| Group E | 2.5x | 1.3x |
| Group F | 2.9x | 1.4x |

Table 1

Stents cut from Groups A and B (uniaxially drawn tubing in either direction) both failed upon balloon expansion on failure planes parallel to the direction of orientation. In Group A these were planes in the axial direction and in Group B these were planes running circumferentially. These planes have force normal components perpendicular to the draw direction and consistent with Example 5, the strength and elongation at break in the normal or perpendicular direction is compromised to some degree by drawing this material. However, all stents biaxially drawn were successfully deployed without cracking with radial strengths ranging from about thirteen to about eighteen psi and acute recoil at about thirteen to about fifteen percent.

Figure 2:
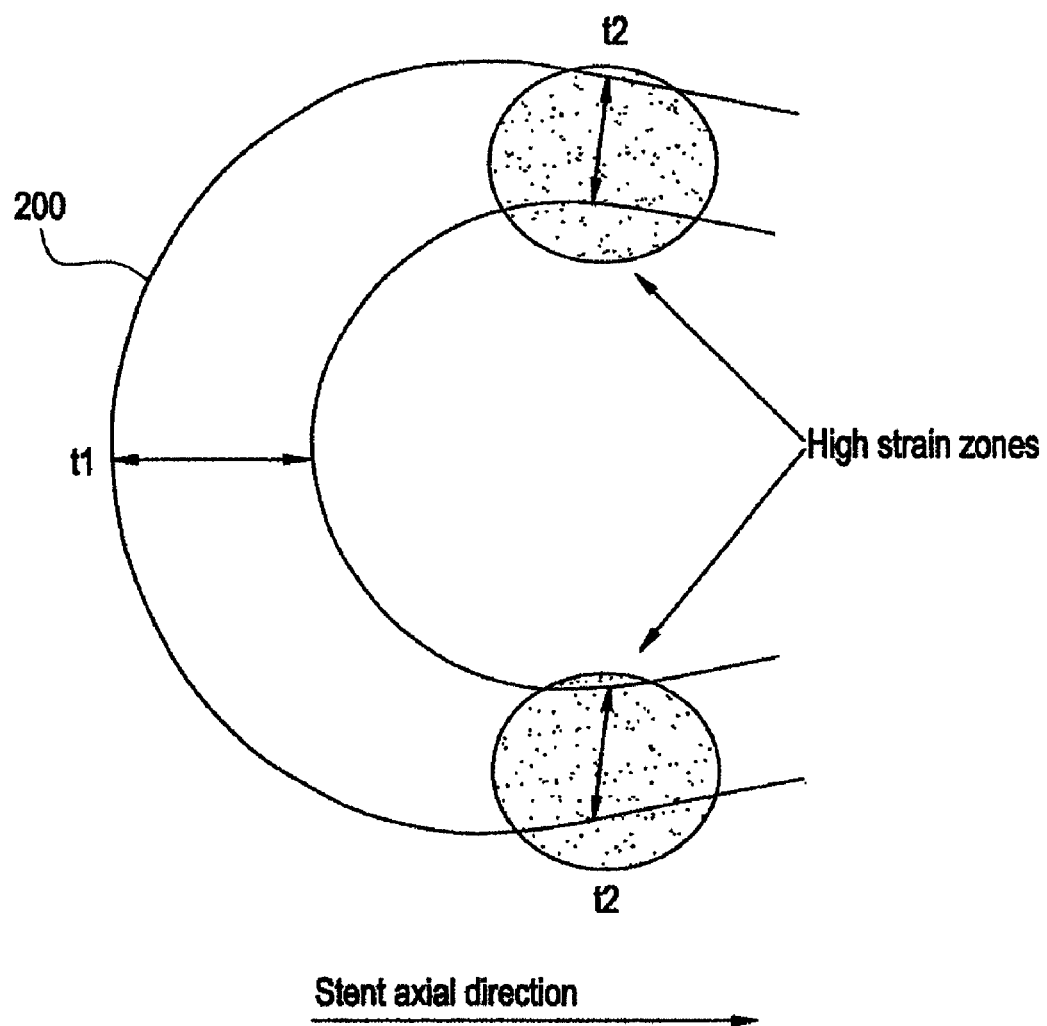
FIG. 2 is a representation of a section of hoop component of an exemplary stent that demonstrates two high strain zones to accommodate axial orientation.

Referring to FIG. 2, there is illustrated a section 200 of a hoop component 102 formed from a polymeric material as described herein. As illustrated, the section 200 of the hoop component 102 is designed to have two first zones t2 and one second zone t1. The two zones, t2, are designed or configured to have a greater degree of polymer chain orientation compared to the one second zone, t1. The higher degree of polymer chain orientation can be achieved in zones t2 by drawing the precursor material in a direction along the longitudinal axis of the stent, or the axial direction. Additionally, orientation may also be achieved by methods described above. In the exemplary embodiment illustrated in FIG. 2, the t2 regions are thinner than the t1 region by design and because of this, the t2 regions are high strain zones compared to the t1 region. By optimizing the type and degree of polymer chain orientation and feature characteristics, the device performance characteristics may be enhanced. Performance characteristics for hoop components in a stent typically include radial strength, radial stiffness, and radial recoil. In addition, consideration should preferably be given to dynamic loads such as pulsatile motion.

Figure 3:
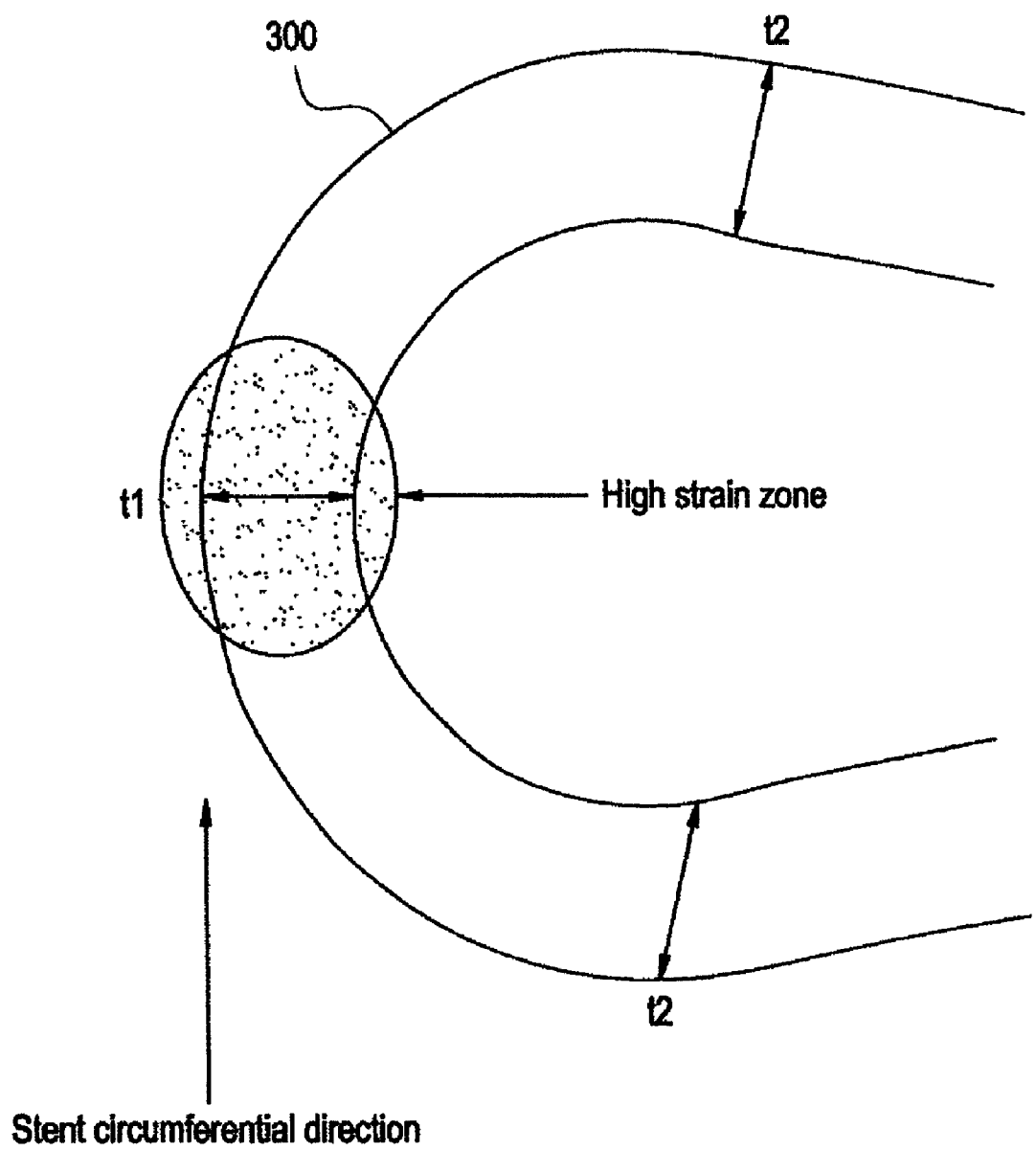
FIG. 3 is a representation of a section of hoop component of an exemplary stent that demonstrates one high strain zone to accommodate circumferential orientation.

Referring to FIG. 3, there is illustrated a section 300 of a hoop component 102 formed from a polymeric material as described herein. As illustrated, the section 300 of the hoop component 102 is designed to have one first zone t1 and two second zones t2. The one zone, t1, is designed or configured to have a greater degree of polymer chain orientation compared to the two second zones, t2. The higher degree of polymer chain orientation may be achieved in zone t1 by drawing the precursor material in a direction along the radial or circumferential axis of the stent. Additionally, orientation may also be achieved by methods described above. In the exemplary embodiment illustrated in FIG. 3, the t1 region is thinner than the t2 regions by design and because of this, the t1 region is a high strain zone compared to the t2 regions. By optimizing the type and degree of polymer chain orientation and feature characteristics, the device performance characteristics may be enhanced. Performance characteristics for hoop components in a stent typically include radial strength, radial stiffness, and radial recoil. In addition, consideration should preferably be given to dynamic loads such as pulsatile motion.

Figure 4:
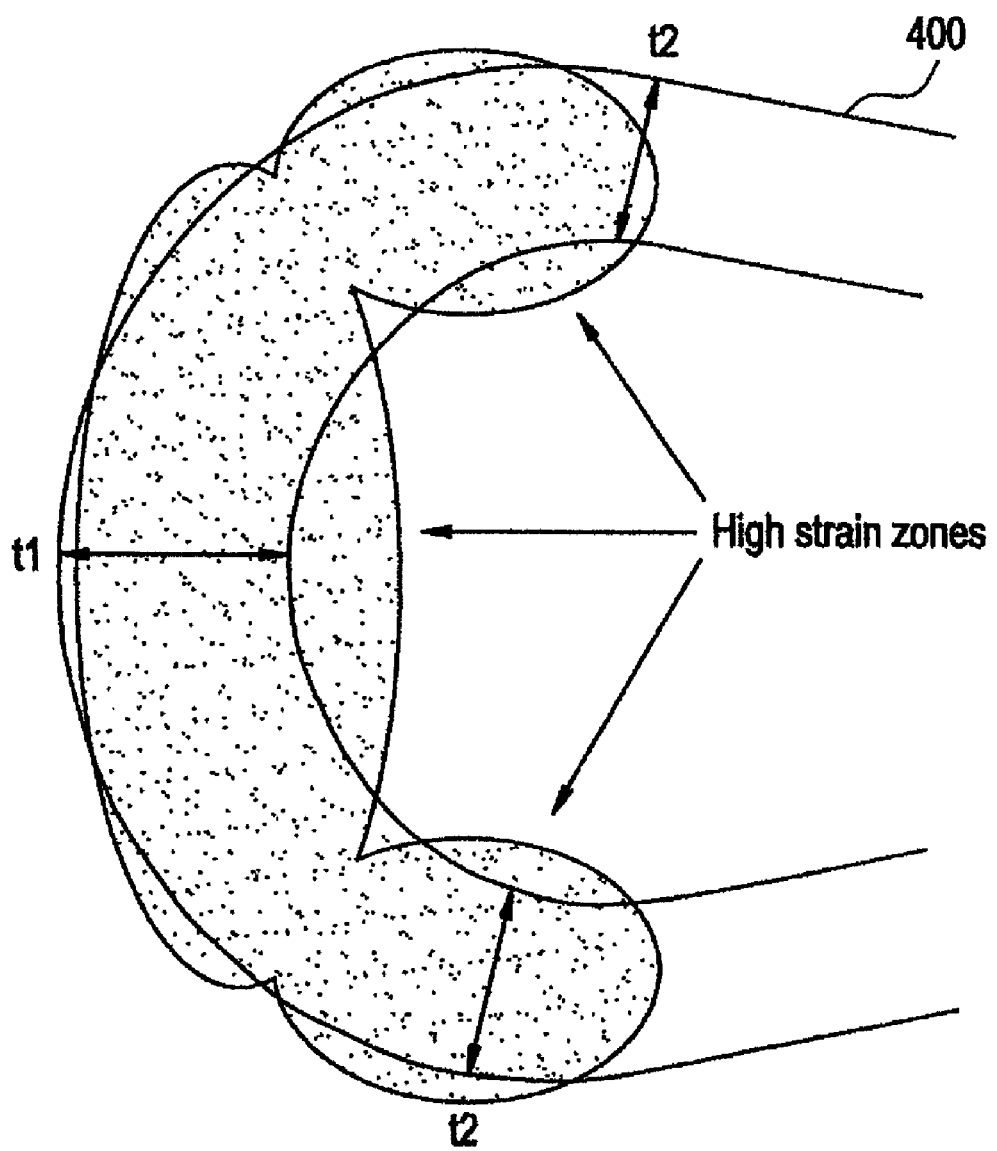
FIG. 4 is a representation of a section of hoop component of an exemplary stent that demonstrates three high strain zones to accommodate biaxial orientation.

In addition, referring to FIG. 4, there is illustrated a section 400 of a hoop component 102 formed from a polymeric material as described herein. This drawing represents the combination of the polymer chain orientations illustrated in FIGS. 2 and 3. In other words, the degree of alignment in zones t1 and t2 may be substantially equal.

Figure 5:
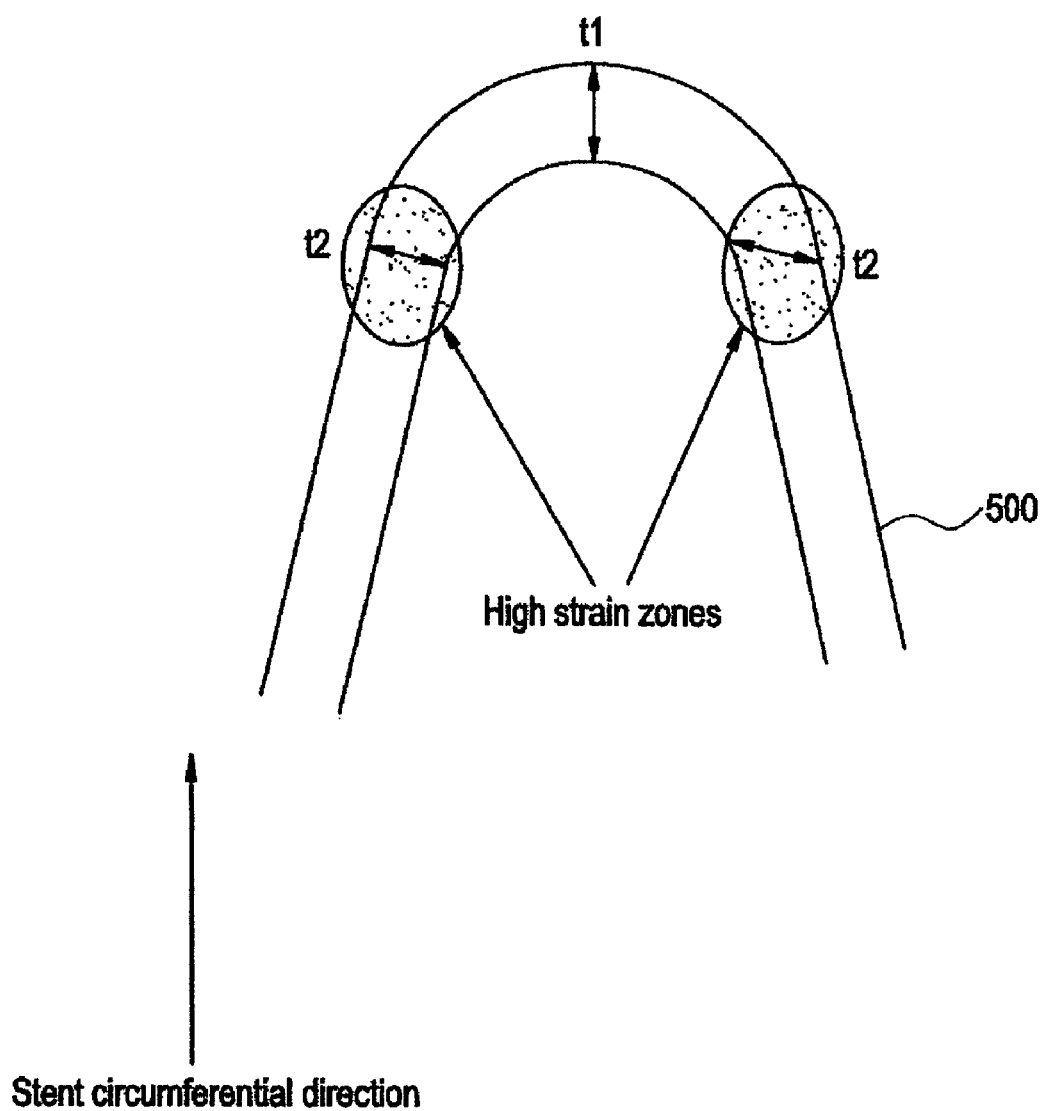
FIG. 5 is a representation of a section of flexible connector component of an exemplary stent that demonstrates two high strain zones to accommodate circumferential orientation.

Referring to FIG. 5, there is illustrated a section 500 of a flexible connector 104 formed from a polymeric material as described herein. As illustrated, the section 500 of the flexible connector 104 is designed to have two first zones t2 and one second zone t1. The two zones, t2, are designed or configured to have a greater degree of polymer chain orientation compared to the one second zone, t1. The higher degree of polymer chain orientation may be achieved in zones t2 by drawing the precursor material in a direction along the radial or circumferential axis of the stent. Additionally, orientation may also be achieved by methods described above. In the exemplary embodiment illustrated in FIG. 5, the t2 regions are thinner than the 51 region by design and because of this, the t2 regions are high strain zones compared to the t1 region. By optimizing the type and degree of polymer chain orientation and feature characteristics, the device performance characteristics may be enhanced. Performance characteristics for flexible connector components in a stent are multiaxial and torsional flexibility in consideration of dynamic loading situations and foreshortening in consideration of deployment.

Figure 6:
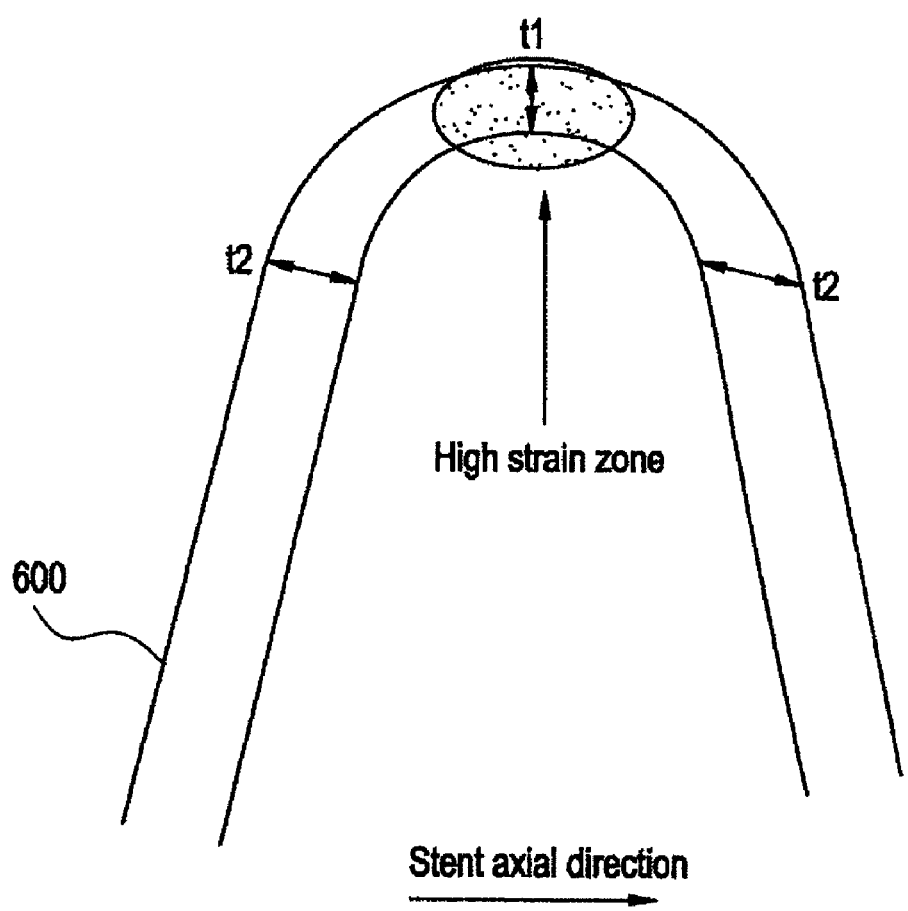
FIG. 6 is a representation of a section of flexible connector component of an exemplary stent that demonstrates one high strain zone to accommodate axial orientation.

Referring to FIG. 6, there is illustrated a section 600 of a flexible connector 104 formed from a polymeric material as described herein. As illustrated, the section 600 of the flexible connector 104 is designed to have one first zone t1 and two second zones t2. The one zone, t1, is designed or configured to have a greater degree of polymer chain orientation compared to the two second zones, t2. The higher degree of polymer chain orientation may be achieved in zone t1 by drawing the precursor material in a direction along the longitudinal axis of the stent. Additionally, orientation may also be achieved by methods described above. In the exemplary embodiment illustrated in FIG. 6, the t1 region is a high strain zone compared to the t2 regions. By optimizing the type and degree of polymer chain orientation and feature characteristics, the device performance characteristics may be enhanced. Performance characteristics for flexible connector components in a stent are multiaxial and torsional flexibility in consideration of dynamic loading situations and foreshortening in consideration of deployment.

Figure 7:
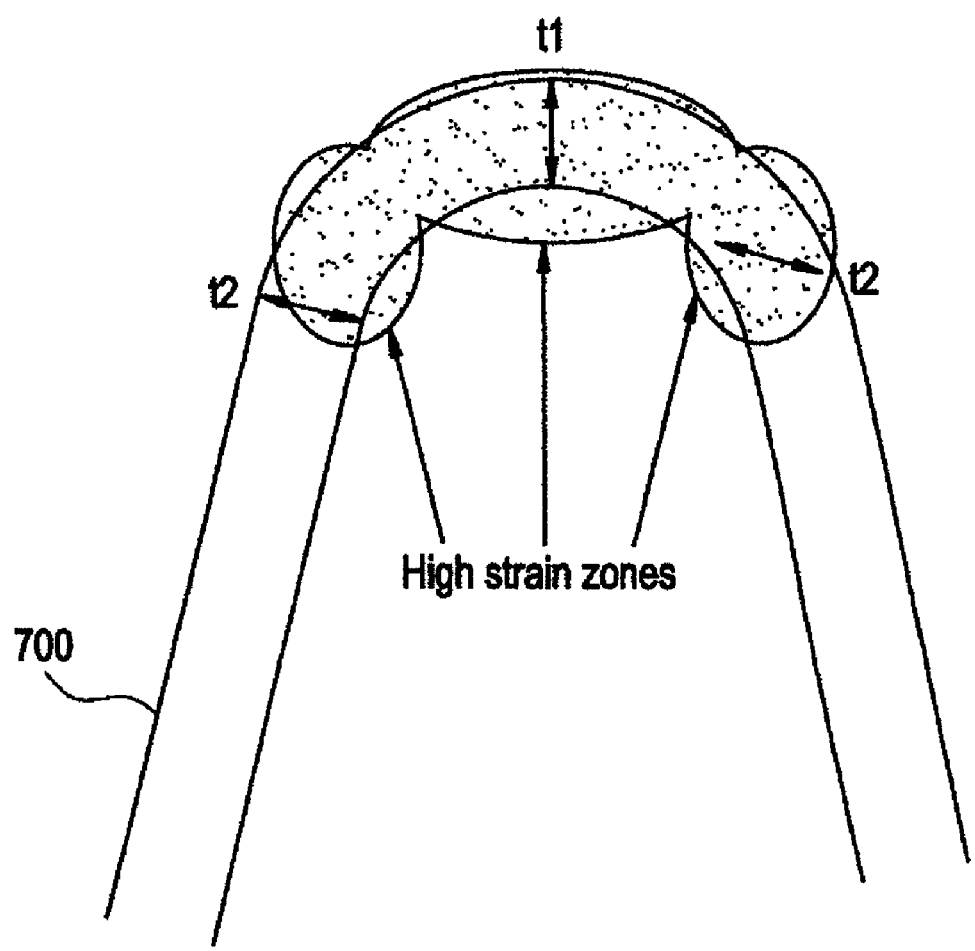
FIG. 7 is a representation of a section of flexible connector component of an exemplary stent that demonstrates three high strain zones to accommodate biaxial orientation.

Referring to FIG. 7, there is illustrated a section 700 of a flexible connector 104 formed from a polymeric material as described herein. This drawing represents the combination of the polymer chain orientations illustrated in FIGS. 5 and 6. In other words, the degree of alignment in zones t1 and t2 may be substantially equal.

To the skilled artisan, there are a multitude of design considerations that will determine which configuration is preferred to achieve optimal stent performance. The figures above merely illustrate a few possibilities. It is appropriate to consider acute and chronic stent performance attributes in order to optimize the design and material combination. One of these factors includes the design of the flexible connector elements. For example, if the flexible connector joins the radial hoops at the apex of the radial arc, the designer may choose the longitudinal component of the radial hoop to contain the high strain region. Optimization of the material and the design would thus result in the preferential longitudinal orientation of the polymer chains. Alternately, if the flexible connectors join the radial hoops at the ends of the radial arcs or in the radial strut sections, the designer may choose the apex of the radial arc to contain the high strain region. Accordingly, in this design optimization of the material and the design would thus result in the preferential circumferential orientation of the polymer chains.

Additionally, if loads on the flexible connector align to the longitudinally oriented elements of the flexible connector, then optimization of the material and design would result in the preferential longitudinal orientation of the polymer chains. Similarly, if loads on the flexible connector align to the circumferentially oriented elements of the flexible connector, then optimization of the material and design would result in the preferential circumferential orientation of the polymer chains.

The above descriptions are merely illustrative and should not be construed to capture all consideration in decisions regarding the optimization of the design and material orientation.

It is important to note that although specific configurations are illustrated and described, the principles described are equally applicable to any configurations of hoop and flexible connector designs. In addition, the axes of alignment may not correspond to a single direction, for example longitudinally or radially, but rather a combination of the two.

Polymeric materials may be broadly classified as synthetic, natural and/or blends thereof. Within these broad classes, the materials may be defined as biostable or biodegradable. Examples of biostable polymers include polyolefins, polyamides, polyesters, fluoropolymers, and acrylics. Examples of natural polymers include polysaccharides and proteins.

Biosorobable polymers consist of bulk and surface erodable materials. Surface erosion polymers are typically hydrophobic with water labile linkages. Hydrolysis tends to occur fast on the surface of such surface erosion polymers with no water penetration in bulk. The initial strength of such surface erosion polymers tends to be low however, and often such surface erosion polymers are not readily available commercially. Nevertheless, examples of surface erosion polymers include polyanhydrides such as poly (carboxyphenoxy hexane-sebacicacid), poly (fumaric acid-sebacic acid), poly (carboxyphenoxy hexane-sebacic acid), poly (imide-sebacic acid) (50-50), poly (imide-carboxyphenoxy hexane-) (33-67), and polyorthoesters (diketene acetal based polymers).

Bulk erosion polymers, on the other hand, are typically hydrophilic with water labile linkages. Hydrolysis of bulk erosion polymers tends to occur at more uniform rates across the polymer matrix of the device. Bulk erosion polymers exhibit superior initial strength and are readily available commercially.

Examples of bulk erosion polymers include poly ($\alpha$-hydroxy esters) such as poly (lactic acid), poly (glycolic acid), poly (caprolactone), poly (p-dioxanone), poly (trimethylene carbonate), poly (oxaesters), poly (oxaamides), and their copolymers and blends. Some commercially readily available bulk erosion polymers and their commonly associated medical applications include poly (dioxanone) [PDS® suture available from Ethicon, Inc., Somerville, N.J.], poly (glycolide) [Dexon® sutures available from United States Surgical Corporation, North Haven, Conn.], poly (lactide)-PLLA [bone repair], poly (lactide/glycolide) [Vicryl® (10/90) and Panacryl® (95/5) sutures available from Ethicon, Inc., Somerville, N.J.], poly (glycolide/caprolactone (75/25) [Monocryl® sutures available from Ethicon, Inc., Somerville, N.J.], and poly (glycolide/trimethylene carbonate) [Maxon® sutures available from United States Surgical Corporation, North Haven, Conn.].

Other bulk erosion polymers are tyrosine derived poly amino acid [examples: poly (DTH carbonates), poly (acrylates), and poly (imino-carbonates)], phosphorous containing polymers [examples: poly (phosphoesters) and poly (phosphazenes)], poly (ethylene glycol) [PEG] based block co-polymers [PEG-PLA, PEG-poly (propylene glycol), PEG-poly (butylene terphthalate)], poly ($\alpha$-malic acid), poly (ester amide), and polyalkanoates [examples: poly (hydroxybutyrate (HB) and poly (hydroxyvalerate) (HV) co-polymers].

Of course, the devices may be made from combinations of surface and bulk erosion polymers in order to achieve desired physical properties and to control the degradation mechanism. For example, two or more polymers may be blended in order to achieve desired physical properties and device degradation rate. Alternatively, the device can be made from a bulk erosion polymer that is coated with a surface erosion polymer.

Shape memory polymers can also be used. Shape memory polymers are characterized as phase segregated linear block co-polymers having a hard segment and a soft segment. The hard segment is typically crystalline with a defined melting point, and the soft segment is typically amorphous with a defined glass transition temperature. The transition temperature of the soft segment is substantially less than the transition temperature of the hard segment in shape memory polymers. A shape in the shape memory polymer is memorized in the hard and soft segments of the shape memory polymer by heating and cooling techniques. Shape memory polymers can be biostable and bioabsorbable. Bioabsorbable shape memory polymers are relatively new and comprise thermoplastic and thermoset materials. Shape memory thermoset materials may include poly (caprolactone)dimethylacrylates, and shape memory thermoplastic materials may include poly (caprolactone) as the soft segment and poly (glycolide) as the hard segment.

In order to provide materials having high ductility and toughness, such as is often required for orthopedic implants, sutures, stents, grafts and other medical applications including drug delivery devices, the bioabsorbable polymeric materials may be modified to form composites or blends thereof. Such composites or blends may be achieved by changing either the chemical structure of the polymer backbone, or by creating composite structures by blending them with different polymers and plasticizers. Any additional materials used to modify the underlying bioabsorbable polymer should preferably be compatible with the main polymer system. The additional materials also tend to depress the glass transition temperature of the bioabsorbable polymer, which renders the underlying polymer more ductile and less stiff.

As an example of producing a composite or blended material, blending a very stiff polymer such as poly (lactic acid), poly (glycolide) and poly (lactide-co-glycolide) copolymers with a soft and ductile polymer such as poly (caprolactone) and poly (dioxanone) tends to produce a material with high ductility and high stiffness. An elastomeric co-polymer can also be synthesized from a stiff polymer and a soft polymer in different ratios. For example, poly (glycolide) or poly (lactide) can be copolymerized with poly (caprolactone) or poly (dioxanone) to prepare poly(glycolide-co-caprolactone) or poly(glycolide-co-dioxanone) and poly(lactide-co-caprolactone) or poly(lactide-co-dioxanone) copolymers. These elastomeric copolymers can then be blended with stiff materials such as poly (lactide), poly (glycolide) and poly (lactide-co-glycolide) copolymers to produce a material with high ductility. Alternatively, terpolymers can also be prepared from different monomers to achieve desired properties. Macromers and other cross-linkable polymer systems may be used to achieve the desired properties.

Because visualization of the device as it is implanted in the patient is important to the medical practitioner for locating the device, radiopaque materials may be added to the device. The radiopaque materials may be added directly to the matrix of bioabsorbable materials comprising the device during processing thereof resulting in fairly uniform incorporation of the radiopaque materials throughout the device. Alternatively, the radiopaque materials may be added to the device in the form of a layer, a coating, a band or powder at designated portions of the device depending on the geometry of the device and the process used to form the device. Coatings can be applied to the device in a variety of processes known in the art such as, for example, chemical vapor deposition (CVD), physical vapor deposition (PVD), electroplating, high-vacuum deposition process, microfusion, spray coating, dip coating, electrostatic coating, or other surface coating or modification techniques. Ideally, the radiopaque material does not add significant stiffness to the device so that the device can readily traverse the anatomy within which it is deployed. The radiopaque material should be biocompatible with the tissue within which the device is deployed. Such biocompatibility minimizes the likelihood of undesirable tissue reactions with the device. Inert noble metals such as gold, platinum, iridium, palladium, and rhodium are well-recognized biocompatible radiopaque materials. Other radiopaque materials include barium sulfate ($BaSO_4$), bismuth subcarbonate $[(BiO)_2CO_3]$ and bismuth oxide. Ideally, the radiopaque materials adhere well to the device such that peeling or delamination of the radiopaque material from the device is minimized, or ideally does not occur. Where the radiopaque materials are added to the device as metal bands, the metal bands may be crimped at designated sections of the device. Alternatively, designated sections of the device may be coated with a radiopaque metal powder, whereas other portions of the device are free from the metal powder.

The local delivery of therapeutic agent/therapeutic agent combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any other type of medical device may be coated in some fashion with a drug or drug combination, which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paditaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine and cytarabine) purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalec), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors, antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with another exemplary embodiment, the stents described herein, whether constructed from metals or polymers, may be utilized as therapeutic agents or drug delivery devices. The metallic stents may be coated with a biostable or bioabsorbable polymer or combinations thereof with the therapeutic agents incorporated therein. Typical material properties for coatings include flexibility, ductility, tackiness, durability, adhesion and cohesion. Biostable and bioabsorbable polymers that exhibit these desired properties include methacrylates, polyurethanes, silicones, poly (vinyl acetate), poly (vinyl alcohol), ethylene vinyl alcohol, poly (vinylidene fluoride), poly (lactic acid), poly (glycolic acid), poly (caprolactone), poly (trimethylene carbonate), poly (dioxanone), polyorthoester, polyanhydrides, polyphosphoester, polyaminoacids as well as their copolymers and blends thereof.

In addition to the incorporation of therapeutic agents, the coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic microspheres as will be described in greater detail subsequently. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

As described above, different drugs may be utilized as therapeutic agents, including sirolimus, heparin, everolimus, tacrolimus, paclitaxel, cladribine as well as classes of drugs such as statins. These drugs and/or agents may be hydrophilic, hydrophobic, lipophilic and/or lipophobic. The type of agent will play a role in determining the type of polymer. The amount of the drug in the coating may be varied depending on a number of factors including, the storage capacity of the coating, the drug, the concentration of the drug, the elution rate of the drug as well as a number of additional factors. The amount of drug may vary from substantially zero percent to substantially one hundred percent. Typical ranges may be from about less than one percent to about forty percent or higher. Drug distribution in the coating may be varied. The one or more drugs may be distributed in a single layer, multiple layers, single layer with a diffusion barrier or any combination thereof.

Different solvents may be used to dissolve the drug/polymer blend to prepare the coating formulations. Some of the solvents may be good or poor solvents based on the desired drug elution profile, drug morphology and drug stability.

There are several ways to coat the stents that are disclosed in the prior art. Some of the commonly used methods include spray coating; dip coating; electrostatic coating; fluidized bed coating; and supercritical fluid coatings.

Some of the processes and modifications described herein that may be used will eliminate the need for polymer to hold the drug on the stent. Stent surfaces may be modified to increase the surface area in order to increase drug content and tissue-device interactions. Nanotechnology may be applied to create self-assembled nanomaterials that can contain tissue specific drug containing nanoparticles. Microstructures may be formed on surfaces by microetching in which these nanoparticles may be incorporated. The microstructures may be formed by methods such as laser micromachining, lithography, chemical vapor deposition and chemical etching. Microstructures have also been fabricated on polymers and metals by leveraging the evolution of micro electro-mechanical systems (MEMS) and microfluidics. Examples of nanomaterials include carbon nanotubes and nanoparticles formed by sol-gel technology. Therapeutic agents may be chemically or physically attached or deposited directly on these surfaces. Combination of these surface modifications may allow drug release at a desired rate. A top-coat of a polymer may be applied to control the initial burst due to immediate exposure of drug in the absence of polymer coating.

As described above, polymer stents may contain therapeutic agents as a coating, e.g. a surface modification. Alternatively, the therapeutic agents may be incorporated into the stent structure, e.g. a bulk modification that may not require a coating. For stents prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable. In addition, with higher concentrations of therapeutic agent or agents, regional drug delivery is achievable for greater durations of time.

In yet another alternate embodiment, the intentional incorporation of ceramics and/or glasses into the base material may be utilized in order to modify its physical properties. Typically, the intentional incorporation of ceramics and/or glasses would be into polymeric materials for use in medical applications. Examples of biostable and/or bioabsorbable ceramics or/or glasses include hydroxyapatite, tricalcium phosphate, magnesia, alumina, zirconia, yttrium tetragonal polycrystalline zirconia, amorphous silicon, amorphous calcium and amorphous phosphorous oxides. Although numerous technologies may be used, biostable glasses may be formed using industrially relevant sol-gel methods. Sol-gel technology is a solution process for fabricating ceramic and glass hybrids. Typically, the sol-gel process involves the transition of a system from a mostly colloidal liquid (sol) into a gel.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed:

1. A substantially tubular intraluminal medical device having a longitudinal axis and a radial axis, the device comprising:
 a plurality of hoops formed from a polymeric material, the plurality of hoops comprising a plurality of radial struts and a plurality of radial arcs, the plurality of radial struts having a first amount of alignment via drawing and annealing of the polymer chains in a direction substantially parallel to the longitudinal axis and the plurality of radial arcs having a second amount of alignment via drawing and annealing of the polymer chains in a direction substantially parallel to the radial axis, the first amount of alignment being greater than the second amount of alignment, and wherein the radial struts are thinner than the radial arcs thereby creating high strain zones in the radial struts relative to the radial arcs; and
 a plurality of bridges formed from a polymeric material interconnecting the plurality of hoops, wherein the substantially tubular intraluminal medical device has a radial strength in the range from about 13 to 18 psi and an acute recoil at about 13 to 15 percent.

2. The substantially tubular intraluminal device according to claim 1, further comprising at least one therapeutic agent.

3. The substantially tubular intraluminal device according to claim 2, wherein the at least one therapeutic agent comprises an antirestenotic agent.

4. The substantially tubular intraluminal device according to claim 3, wherein the antirestenotic agent comprises a rapamycin.

* * * * *